United States Patent
Ning et al.

(10) Patent No.: US 12,155,037 B2
(45) Date of Patent: Nov. 26, 2024

(54) NONAQUEOUS ELECTROLYTE SOLUTION FOR POWER STORAGE DEVICES

(71) Applicant: TOMIYAMA PURE CHEMICAL INDUSTRIES, LTD., Tokyo (JP)

(72) Inventors: Tailu Ning, Kamisu (JP); Kazuyuki Shimizu, Kamisu (JP); Hiroo Nitta, Kamisu (JP)

(73) Assignee: TOMIYAMA PURE CHEMICAL INDUSTRIES, LTD., Tokyo (JP)

( * ) Notice: Subject to any disclaimer, the term of this patent is extended or adjusted under 35 U.S.C. 154(b) by 1025 days.

(21) Appl. No.: 16/981,834

(22) PCT Filed: Mar. 23, 2018

(86) PCT No.: PCT/JP2018/011834
§ 371 (c)(1),
(2) Date: Sep. 17, 2020

(87) PCT Pub. No.: WO2019/180946
PCT Pub. Date: Sep. 26, 2019

(65) Prior Publication Data
US 2021/0043973 A1    Feb. 11, 2021

(51) Int. Cl.
| | |
|---|---|
| *H01M 10/0567* | (2010.01) |
| *C07C 317/18* | (2006.01) |
| *H01M 10/0525* | (2010.01) |
| *H01M 10/0568* | (2010.01) |
| *H01M 10/0569* | (2010.01) |

(52) U.S. Cl.
CPC ....... *H01M 10/0567* (2013.01); *C07C 317/18* (2013.01); *H01M 10/0525* (2013.01); *H01M 10/0568* (2013.01); *H01M 10/0569* (2013.01); *H01M 2300/004* (2013.01)

(58) Field of Classification Search
CPC ......... H01M 10/0567; H01M 10/0525; H01M 10/0568; H01M 10/0569; H01M 2300/004; C07C 317/18
See application file for complete search history.

(56) References Cited

U.S. PATENT DOCUMENTS

| | | |
|---|---|---|
| 2002/0015894 A1 | 2/2002 | Wariishi et al. |
| 2003/0013021 A1 | 1/2003 | Wariishi |
| 2010/0068613 A1* | 3/2010 | Deguchi ............. H01M 50/414 429/129 |
| 2010/0092872 A1 | 4/2010 | Abe et al. |

FOREIGN PATENT DOCUMENTS

| | | |
|---|---|---|
| CN | 103094613 A | 5/2013 |
| JP | 2000017076 A | 1/2000 |
| JP | 2015173107 A | 10/2015 |
| JP | 2017168347 A | 9/2017 |
| WO | WO-2008133112 A1 | 11/2008 |

OTHER PUBLICATIONS

International Preliminary Report on Patentability and Written Opinion issued Sep. 29, 2020 in PCT/JP2018/011834 (English translation only).
International Search Report issued May 15, 2018 in PCT/JP2018/011834 (with English translation), 5 pages.
Extended European Search Report issued Sep. 30, 2021 in Patent Application No. 18911178.4, 9 pages.
Feng Wu et al, "Toward 5 V Li-Ion Batteries: Quantum Chemical Calculation and Electrochemical Characterization of Sulfone-Based High-Voltage Electrolytes", Applied Materials & Interfaces, American Chemical Society, 2015, pp. 15098-15107.

\* cited by examiner

*Primary Examiner* — Brian R Ohara
*Assistant Examiner* — Emily Elizabeth Freeman
(74) *Attorney, Agent, or Firm* — Element IP, PLC

(57) ABSTRACT

To provide a non-aqueous electrolytic solution for a storage device, which can reduce the electric resistance, which is excellent in cycle properties, and which can suppress gas generation by the reaction of the non-aqueous electrolytic solution, and a storage device.
A non-aqueous electrolytic solution for a storage device having an electrolyte dissolved in a non-aqueous solvent, wherein the electrolyte is a lithium salt soluble in the non-aqueous solvent, and the non-aqueous electrolytic solution contains an organic sulfone compound represented by the following formula (1):

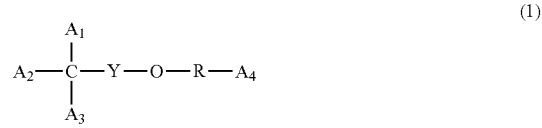

wherein the symbols are as defined in the description.

12 Claims, No Drawings

NONAQUEOUS ELECTROLYTE SOLUTION FOR POWER STORAGE DEVICES

TECHNICAL FIELD

The present invention relates to a non-aqueous electrolytic solution for a storage device such as a lithium ion secondary battery.

BACKGROUND ART

In recent years, as various portable electronic equipment such as portable electronic terminals represented by mobile phones and notebook computers are widely used, a secondary battery plays an important role as their power source. As such a secondary battery, an aqueous battery such as a lead-acid battery and a nickel-cadmium battery, and a non-aqueous electrolyte battery may be mentioned. Particularly, a non-aqueous electrolyte secondary battery comprising a positive electrode and a negative electrode capable of absorbing and desorbing lithium ions, and a non-aqueous electrolytic solution provides a high energy density at a high voltage, is excellent in safety and has various advantages as compared with other secondary batteries in view of environmental problem, etc.

As a non-aqueous electrolyte secondary battery practically used at present, for example, a lithium ion secondary battery using as a cathode active material a composite oxide of lithium and a transition metal, as an anode active material a material capable of doping and undoping lithium ions may be mentioned. As an anode active material for a lithium ion secondary battery providing excellent cycle properties, a carbon material may be mentioned.

Further, as such a non-aqueous electrolytic solution, a non-aqueous solution having a lithium salt such as $LiBF_4$, $LiPF_6$, $LiClO_4$, $LiN(SO_2CF_3)_2$ or $LiN(SO_2CF_2CF_3)_2$ mixed with an aprotic organic solvent has been used. The non-aqueous electrolytic solution is required to lower the electric resistance to improve the lithium ion conductivity, and to suppress the decrease of the battery capacity and maintain a high capacity even after charging and discharging are repeatedly carried out, thereby to improve so-called cycle properties, thus prolonging the life.

Further, the non-aqueous electrolytic solution, if exposed to high temperature in a charged state, is likely to react with the composite oxide of lithium and a transition metal and to gas, and as a result, to lead to swelling of the battery and capacity deterioration resulting from increase of the internal resistance. Accordingly, development of a non-aqueous electrolytic solution with a small amount of gas generation at high temperature is desired.

Patent Document 1 discloses a non-aqueous electrolytic solution for a storage device having a lithium salt dissolved in a non-aqueous solvent, which contains an organic sulfone compound represented by the following formula (2):

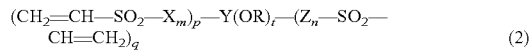

wherein X, Y and Z are each independently a phenylene group or a $C_{1-4}$ alkylene group, R is a hydrogen atom, a phenyl group or a $C_{1-6}$ alkyl group, m, n, p, q and t are each independently an integer of 0 or from 1 to 4, p+q≥1, and m+n≥1.

According to the non-aqueous electrolytic solution of Patent Document 1, as compared with conventional technique, the electrical resistance of the non-aqueous electrolytic solution can be decreased, and in addition, a high capacity can be maintained even after charging and discharging are repeatedly carried out, however, further improvement in properties of the non-aqueous electrolytic solution has been desired.

PRIOR ART DOCUMENTS

Patent Documents

Patent Document 1: JP-A-2017-168347

DISCLOSURE OF INVENTION

Technical Problem

The object of the present invention is to provide a non-aqueous electrolytic solution for a storage device, of which the electric resistance can be decreased, which can maintain a high capacity even after charging and discharging are repeatedly carried out many times, and which can suppress gas generation by the reaction of the non-aqueous electrolytic solution.

Solution to Problem

The present inventors have conducted extensive studies and as a result, found that the non-aqueous electrolytic solution which contains an organic sulfone compound represented by the following formula (1) is very effective to achieve the above object, and accomplished the present invention.

That is, the present invention provides the following.

1. A non-aqueous electrolytic solution for a storage device having an electrolyte dissolved in a non-aqueous solvent, wherein the electrolyte is a lithium salt soluble in the non-aqueous solvent, and the non-aqueous electrolytic solution contains an organic sulfone compound represented by the following formula (1):

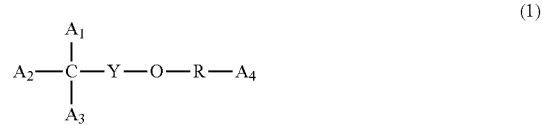

wherein $A_1$, $A_2$, $A_3$ and $A_4$ are each independently —X—$SO_2$—CH=$CH_2$, a hydrogen atom, a substituted or non-substituted $C_{1-5}$ alkyl group, alkenyl group, alkynyl group or alkoxy group, a substituted or non-substituted $C_{6-10}$ aryl group, or —O—$SiR'_1R'_2R'_3$ (wherein $R'_1$, $R'_2$ and $R'_3$ are each independently a hydrogen atom, a substituted or non-substituted $C_{1-5}$ alkyl group), provided that at least one of $A_1$, $A_2$, $A_3$ and $A_4$ is —X—$SO_2$—CH=$CH_2$, X and Y are each independently a single bond, a substituted or non-substituted phenylene group, or a substituted or non-substituted $C_{1-4}$ alkylene group, R is selected from the following groups:

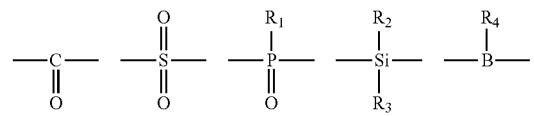

wherein $R_1$, $R_2$, $R_3$ and $R_4$ are each independently a hydrogen atom, a substituted or non-substituted $C_{1-5}$ alkyl group, alkenyl group, alkynyl group or alkoxy group, a substituted or non-substituted $C_{6-10}$ aryl group, or —O—$SiR'_1R'_2R'_3$ (wherein $R'_1$, $R'_2$ and $R'_3$ are as defined above).

2. The non-aqueous electrolytic solution for a storage device according to 1, wherein R in the formula (1) is selected from the following groups:

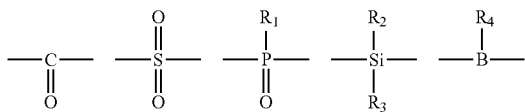

wherein $R_1$ is a substituted or non-substituted $C_{1-5}$ alkyl group, alkenyl group, alkynyl group or alkoxy group, or —O—$SiR'_1R'_2R'_3$ (wherein $R'_1$, $R'_2$ and $R'_3$ are as defined above), and $R_2$ and $R_3$ are each independently a substituted or non-substituted $C_{1-5}$ alkyl group or alkoxy group, or a vinyl group, and $R_4$ is s substituted or non-substituted $C_{1-5}$ alkyl group, alkenyl group, alkynyl group or alkoxy group, or —O—$SiR'_1R'_2R'_3$ (wherein $R'_1$, $R'_2$, and $R'_3$ are as defined above).

3. The non-aqueous electrolytic solution for a storage device according to 1 or 2, wherein $A_1$ and $A_2$ are —X—$SO_2$—CH=$CH_2$.

4. The non-aqueous electrolytic solution for a storage device according to any one of 1 to 3, wherein Y is a single bond.

5. The non-aqueous electrolytic solution for a storage device according to any one of 1 to 4, wherein X is a substituted or non-substituted $C_{1-4}$ alkylene group.

6. The non-aqueous electrolytic solution for a storage device according to any one of 1 to 5, which contains from 0.0001 to 10 mass % of the organic sulfone compound.

7. The non-aqueous electrolytic solution for a storage device according to any one of 1 to 6, wherein the non-aqueous solvent contains a chain carbonic acid ester, a saturated cyclic carbonic acid ester and an unsaturated cyclic carbonic acid ester.

8. The non-aqueous electrolytic solution for a storage device according to 7, which has chain carbonic acid ester, saturated cyclic carbonic acid ester and unsaturated cyclic carbonic acid ester contents of from 30 to 80 mass %, from 10 to 50 mass % and from 0.01 to 5 mass %, respectively.

9. The non-aqueous electrolytic solution for a storage device according to any one of 1 to 8, wherein the lithium salt is at least one lithium salt selected from the group consisting of $LiPF_6$, $LiBF_4$, $LiCF_3SO_3$, $LiN(FSO_2)_2$, $LiN(CF_3SO_2)_2$, $LiN(C_2F_5SO_2)_2$, $LiN(CF_3SO_2)(C_2F_5SO_2)$ and $LiN(CF_3SO_2)(C_4F_9SO_2)$.

10. The non-aqueous electrolytic solution for a storage device according to any one of 1 to 9, which further contains at least one additive selected from the group consisting of a sulfur-containing compound (excluding the organic sulfone compound represented by the formula (1)), a cyclic acid anhydride, a carboxylic acid compound, a silicon-containing compound and a boron-containing compound.

11. A storage device using the non-aqueous electrolytic solution as defined in any one of 1 to 10.

12. The storage device according to 11, which is a lithium secondary battery.

Advantageous Effects of Invention

The non-aqueous electrolytic solution of the present invention can decrease the electric resistance, can maintain a high capacity even after charging and discharging are repeatedly carried out many times, and can suppress gas generation by the reaction of the non-aqueous electrolytic solution.

DESCRIPTION OF EMBODIMENTS

<Non-Aqueous Solvent>

As the non-aqueous solvent used for the non-aqueous electrolytic solution of the present invention, various solvents may be used. For example, an aprotic polar solvent is preferred. As specific examples thereof, cyclic carbonates such as ethylene carbonate, propylene carbonate, 1,2-butylene carbonate, 2,3-butylene carbonate, 1,2-pentylene carbonate, 2,3-pentylene carbonate, trifluoromethylethylene carbonate, fluoroethylene carbonate and 4,5-difluoroethylene carbonate; lactones such as γ-butyrolactone and γ-valerolactone; cyclic sulfones such as sulfolane; cyclic ethers such as tetrahydrofuran and dioxane; chain carbonates such as ethyl methyl carbonate, dimethyl carbonate, diethyl carbonate, methyl propyl carbonate, methyl isopropyl carbonate, dipropyl carbonate, methyl butyl carbonate, dibutyl carbonate, ethyl propyl carbonate and methyl trifluoroethyl carbonate; nitriles such as acetonitrile; chain ethers such as dimethyl ether; chain carboxylic acid esters such as methyl propionate; chain glycol ethers such as dimethoxyethane; and fluorinated ethers such as 1,1,2,2-tetrafluoroethyl-2,2,3,3-tetrafluoropropyl ether ($CF_2HCF_2CH_2OCF_2CF_2H$), 1,1,2,2-tetrafluoroethyl-2,2,3,3,3-pentafluoropropyl ether ($CF_3CF_2CH_2OCF_2CF_2H$) and ethoxy-2,2,2-trifluoroethyoxy-ethane ($CF_3CH_2OCH_2CH_2OCH_2CH_3$) may be mentioned. They may be used alone or in combination of two or more.

The non-aqueous solvent is, from the viewpoint of ion conductivity, more preferably a carbonate solvent such as a cyclic carbonate or a chain carbonate. It is more preferred to use, as the carbonate solvent, the cyclic carbonate and the chain carbonate in combination. The cyclic carbonate is, among the above, preferably ethylene carbonate, propylene carbonate or fluoroethylene carbonate. The chain carbonate is, among the above, preferably ethyl methyl carbonate, dimethyl carbonate or diethyl carbonate. When the carbonate solvent is used, with a view to improving battery properties, as the case requires, other non-aqueous solvent such as a nitrile compound or a sulfone compound may further be added.

In the present invention, it is particularly preferred to use, as the non-aqueous solvent, a chain carbonic acid ester, a saturated cyclic carbonic acid ester or an unsaturated cyclic carbonic acid ester. It is particularly preferred to use the three types of the carbonic acid esters, whereby the effects of the present invention are obtained.

As the non-aqueous solvent used in the present invention, in the non-aqueous electrolytic solution, the chain carbonic acid ester, the saturated cyclic carbonic acid ester and the unsaturated cyclic carbonic acid ester are contained preferably in contents of from 30 to 80 mass %, from 10 to 50 mass % and from 0.01 to 5 mass %, respectively, more preferably from 50 to 70 mass %, from 20 to 30 mass % and from 0.1 to 2 mass %.

If the content of the chain carbonic acid ester is lower than 30 mass %, the electrolytic solution tends to have an increased viscosity and in addition solidify at low temperature and thereby exhibits no sufficient properties. On the other hand, if it is higher than 80 mass %, the degree of dissociation/solubility of the lithium salt decreases, and the ion conductivity of the electrolytic solution decreases. If the content of the saturated cyclic carbonic acid ester is lower than 10 mass %, the degree of dissociation/solubility of the lithium salt decreases, and the ion conductivity of the electrolytic solution decreases. On the other hand, if the content is higher than 50 mass %, the viscosity of the electrolytic solution tends to have an increased viscosity and in addition solidify at low temperature and thereby exhibits no sufficient properties.

Further, if the content of the unsaturated cyclic carbonic acid ester is lower than 0.01 mass %, no favorable coating film will be formed on the surface of the negative electrode, and cycle properties tend to deteriorate. On the other hand, if the content is higher than 5 mass %, the electrolytic solution tends to gas when stored at high temperature and the pressure in the battery tends to increase, such being practically unfavorable.

The chain carbonic acid ester used in the present invention may, for example, be a $C_{3-9}$ chain carbonate. It may, for example, be specifically dimethyl carbonate, diethyl carbonate, methyl ethyl carbonate, di-n-propyl carbonate, diisopropyl carbonate, n-propyl isopropyl carbonate, di-n-butyl carbonate, di-t-butyl carbonate, n-butyl isobutyl carbonate, n-butyl-t-butyl carbonate, isobutyl-t-butyl carbonate, ethyl methyl carbonate, methyl-n-propyl carbonate, n-butyl methyl carbonate, isobutyl methyl carbonate, t-butyl methyl carbonate, ethyl-n-propyl carbonate, n-butyl ethyl carbonate, isobutyl ethyl carbonate, t-butyl ethyl carbonate, n-butyl-n-propyl carbonate, isobutyl-n-propyl carbonate, t-butyl-n-propyl carbonate, n-butyl isopropyl carbonate, isobutyl isopropyl carbonate or t-butyl isopropyl carbonate. Among them, the chain carbonic aid ester is preferably dimethyl carbonate, diethyl carbonate or methyl ethyl carbonate, but it is not particularly limited thereto. Such chain carbonic acid esters may be used as a mixture of two or more.

As the saturated cyclic carbonic acid ester used in the present invention, for example, ethylene carbonate, propylene carbonate, butylene carbonate and fluoroethylene carbonate may be mentioned. Among them, ethylene carbonate, propylene carbonate and fluoroethylene carbonate are more preferred. By using propylene carbonate, a non-aqueous electrolytic solution stable at a wider temperature range can be provided. Such saturated cyclic carbonic acid esters may be used as a mixture of two or more.

Further, as the unsaturated cyclic carbonic acid ester used in the present invention, a vinylene carbonate derivative represented by the following formula (3) may be mentioned.

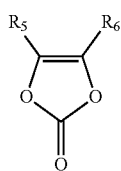

(3)

In the formula (3), $R_5$ and $R_6$ are each independently a hydrogen atom, a halogen atom, or a $C_{1-12}$ alkyl group which may contain a halogen atom. It is preferred that $R_5$ and $R_6$ are a hydrogen atom (that is, the compound of the formula (3) is vinylene carbonate).

As specific examples of the vinylene carbonate derivative, vinylene carbonate, fluorovinylene carbonate, methylvinylene carbonate, fluoromethylvinylene carbonate, ethylvinylene carbonate, propylvinylene carbonate, butylvinylene carbonate, dimethylvinylene carbonate, diethylvinelene carbonate and dipropylvinylene carbonate may be mentioned, but the vinylene carbonate derivative is not limited thereto.

Among these compounds, vinylene carbonate is effective and is economically effective also. Such vinylene carbonate derivatives may be used alone or as a mixture.

As other unsaturated cyclic carbonic acid ester used in the present invention, an alkenylethylene carbonate represented by the following formula (4) may be mentioned.

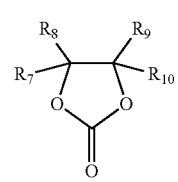

(4)

In the above formula (4), $R_7$ to $R_{10}$ are each independently a hydrogen atom, a halogen atom, a $C_{1-12}$ hydrocarbon group which may contain a halogen atom, or a $C_{2-12}$ alkenyl group, and at least one of them is a $C_{2-12}$ alkenyl group. Particularly, an alkenylethylene carbonate wherein at least one of $R_7$ to $R_{10}$ is a vinyl group and the other is a hydrogen atom is preferred (that is the compound of the formula (4) is 4-vinylethylene carbonate).

As specific examples of the alkenylethylene carbonate, 4-vinylethylene carbonate, 4-vinyl-4-methylethylene carbonate, 4-vinyl-4-ethylethylene carbonate and 4-vinyl-4-n-propylethylene carbonate may be mentioned.

The non-aqueous solvent used in the present invention may further contain, in addition to the above component, other solvent. Such other solvent may, for example, be a cyclic carboxylic acid ester, a $C_{3-9}$ chain ester, or a $C_{3-6}$ chain ether. The content of such other solvent is preferably from 0.2 to 10 mass %, particularly preferably from 0.5 to 5 mass % in the non-aqueous electrolytic solution.

Among the cyclic carboxylic acid esters, as a $C_{3-9}$ lactone compound, for example, γ-butyrolactone, γ-valerolactone, γ-caprolactone and ε-caprolactone may be mentioned. Among them, γ-butyrolactone and γ-valerolactone are more preferred, however, the lactone is not particularly limited. Such cyclic carboxylic acid esters may be used as a mixture of two or more.

As the $C_{3-9}$ chain ester, for example, methyl acetate, ethyl acetate, n-propyl acetate, isopropyl acetate, n-butyl acetate, isobutyl acetate, t-butyl acetate, methyl propionate, ethyl propionate, n-propyl propionate, isopropyl propionate, n-butyl propionate, isobutyl propionate and t-butyl propionate may be mentioned. Among them, ethyl acetate, methyl propionate and ethyl propionate are preferred.

Further, as the $C_{3-6}$ chain ether, dimethoxymethane, dimethoxyethane, diethoxymethane, diethoxyethane, ethoxymethoxymethane and ethoxymethoxyethane may, for example, be mentioned. Among them, dimethoxyethane and diethoxyethane are more preferred.

Further, benzonitrile, acetonitrile, tetrahydrofuran, 2-methyltetrahydrofuran, dioxolane, 4-methyldioxolane, N,N-dimethylformamide, dimethylacetamide, dimethyl sulfoxide, dioxane, sulfolane, dichloroethane, chlorobenzene, nitrobenzene and the like may be used.

<Lithium Salt>

As the solute in the non-aqueous electrolytic solution of the present invention, a lithium salt may be used. The lithium salt is not particularly limited so long as it is soluble in the non-aqueous solvent. Specific examples of such a lithium salt are as follows.

(A) Inorganic Lithium Salts:

Inorganic fluoride salts such as $LiPF_6$, $LiAsF_6$ and $LiBF_4$, perhalogen acid salts such as $LiClO_4$, $LiBrO_4$ and $LiIO_4$, etc.

(B) Organic Lithium Salts:

Organic sulfonates such as $LiCF_3SO_3$; perfluoroalkylsulfonic acid imide salts such as $LiN(FSO_2)_2$, $LiN(CF_3SO_2)_2$, $LiN(C_2F_5SO_2)_2$ and $LiN(CF_3SO_2)(C_4F_9SO_2)$; perfluoroalkylsulfonic acid methide salts such as $LiC(CF_3SO_2)_3$; inorganic fluoride fluorophosphates having some of fluorine atoms substituted with a perfluoroalkyl group, such as $LiPF_5(CF_3)_5$, $LiPF_2(CF_3)_4$, $LiPF_3(CF_3)_3$, $LiPF_2(C_2F_5)_4$, $LiPF_3(C_2F_5)_3$, $LiPF(n-C_3F_7)_5$, $LiPF_2(n-C_3F_7)_4$, $LiPF_3(n-C_3F_7)_3$, $LiPF(iso-C_3F_7)_5$, $LiPF_2(iso-C_3F_7)_4$, $LiPF_3(iso-C_3F_7)_3$, $LiB(CF_3)_4$, $LiBF(CF_3)_3$, $LiBF_2(CF_3)_2$, $LiBF_3(CF_3)$, $LiB(C_2F_5)_4$, $LiBF(C_2F_5)_3$, $LiBF_2(C_2F_5)_2$, $LiBF_3(C_2F_5)$, $LiB(n-C_3F_7)_4$, $LiBF(n-C_3F_7)_3$, $LiBF_2(n-C_3F_7)_2$, $LiBF_3(n-C_3F_7)$, $LiB(iso-C_3F_7)_4$, $LiBF(iso-C_3F_7)_3$, $LiBF_2(iso-C_3F_7)_2$ and $LiBF_3(iso-C_3F_7)$, and fluorinated organic lithium salts of a perfluoroalkyl.

In the present invention, among them, $LiPF_6$, $LiBF_4$, $LiN(CF_3SO_2)_2$, $LiN(C_2F_5SO_2)_2$, $LiN(CF_3SO_2)(C_2F_5SO_2)$ and $LiN(CF_3SO_2)(C_4F_9SO_2)$ are more preferred. Such lithium salts may be used as a mixture of two or more.

The concentration of the lithium salt as the solute of the non-aqueous electrolytic solution of the present invention is preferably from 0.5 to 3 mol/L, more preferably from 0.7 to 2 mol/L. If the concentration is too low, ion conductivity of the non-aqueous electrolytic solution is insufficient due to absolute concentration insufficiency. If the concentration is too high, ion conductivity will decrease due to increase of the viscosity, and deposition at low temperature tends to occur, whereby performance of the non-aqueous electrolyte battery tends to decrease.

<Organic Sulfone Compound>

The non-aqueous electrolytic solution of the present invention contains an organic sulfone compound represented by the following formula (1):

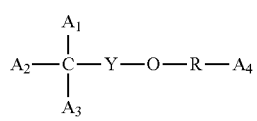

(1)

wherein $A_1$, $A_2$, $A_3$ and $A_4$ are each independently —X—SO$_2$—CH=CH$_2$, a hydrogen atom, a substituted or non-substituted $C_{1-5}$ alkyl group, alkenyl group, alkynyl group or alkoxy group, a substituted or non-substituted $C_{6-10}$ aryl group, or —O—SiR'$_1$R'$_2$R'$_3$ (wherein R'$_1$, R'$_2$ and R'$_3$ are each independently a hydrogen atom, a substituted or non-substituted $C_{1-5}$ alkyl group), provided that at least one of $A_1$, $A_2$, $A_3$ and $A_4$ is —X—SO$_2$—CH=CH$_2$, X and Y are each independently a single bond, a substituted or non-substituted phenylene group, or a substituted or non-substituted $C_{1-4}$ alkylene group, R is selected from the following groups:

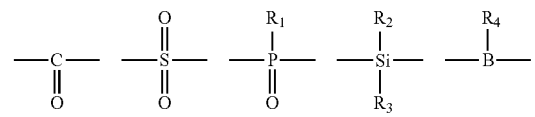

wherein $R_1$, $R_2$, $R_3$ and $R_4$ are each independently a hydrogen atom, a substituted or non-substituted $C_{1-5}$ alkyl group, alkenyl group, alkynyl group or alkoxy group, a substituted or non-substituted $C_{6-10}$ aryl group, or —O—SiR'$_1$R'$_2$R'$_3$ (wherein R'$_1$, R'$_2$ and R'$_3$ are as defined above).

Particularly, R in the formula (1) is preferably selected from the following groups:

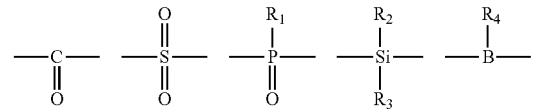

wherein $R_1$ is a substituted or non-substituted $C_{1-5}$ alkyl group, alkenyl group, alkynyl group or alkoxy group, or —O—SiR'$_1$R'$_2$R'$_3$ (wherein R'$_1$, R'$_2$ and R'$_3$ are as defined above), and $R_2$ and $R_3$ are each independently a substituted or non-substituted $C_{1-5}$ alkyl group or alkoxy group, or a vinyl group, and $R_4$ is s substituted or non-substituted $C_{1-5}$ alkyl group, alkenyl group, alkynyl group or alkoxy group, or —O—SiR'$_1$R'$_2$R'$_3$ (wherein R'$_1$, R'$_2$, and R'$_3$ are as defined above).

$A_1$ and $A_2$ are preferably —X—SO$_2$—CH=CH$_2$.

$A_4$ is preferably —X—SO$_2$—CH=CH$_2$.

X is preferably a substituted or non-substituted $C_{1-4}$ alkylene group, more preferably a substituted or non-substituted $C_{1-2}$ alkylene group.

Y is preferably a single bond.

The substituent in each of $A_1$, $A_2$, $A_3$, $A_4$, $R_1$, $R_2$, $R_3$, $R_4$, R'$_1$, R'$_2$, R'$_3$, X and Y may, for example, be a halogen atom such as a fluorine atom, a chlorine atom, a bromine atom or an iodine atom, a hydroxy group, an alkoxy group, an acyl group, an acyloxy group or a carboxy group. The substituent is preferably a fluorine atom.

As preferred specific examples of the organic sulfone compound represented by the formula (1), the following may be mentioned.

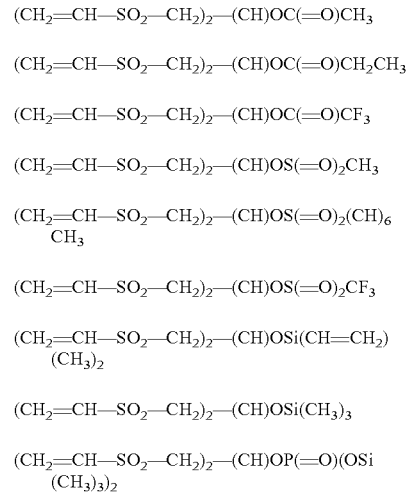

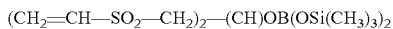

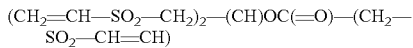

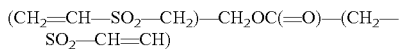

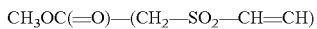

The organic sulfone compound represented by the formula (1) may be produced by a known method. For example, it may be produced by reacting a compound having a hydroxy group and a vinylsulfonyl group, with a corresponding acid anhydride or a corresponding halogen compound.

The content of the organic sulfone compound represented by the formula (1) in the non-aqueous electrolytic solution of the present invention is preferably from 0.0001 to 10 mass %, more preferably from 0.001 to 2 mass %, particularly preferably from 0.01 to 1 mass %. If the content is less than 0.0001 mass %, the effect to reduce the resistance tends to be low. On the other hand, if it exceeds 10 mass %, the coating film resistance tends to be high, and the life will be deteriorated.

<Additive>

The non-aqueous electrolytic solution of the present invention may contain, in addition to the specific organic sulfone compound, an additive, so as to improve the life and the resistance of the storage device. As such an additive, at least one compound selected from the group consisting of a sulfur-containing compound (excluding the organic sulfone compound represented by the formula (1)), a cyclic acid anhydride, a carboxylic acid compound and a boron-containing compound may be used. It is considered that by using an additive having a decomposition potential different from the compound of the present invention, a coating film with less defects can be formed on the surface of the cathode active material and the anode active material, whereby the life and the resistance of the storage device can be improved.

As the sulfur-containing compound, 1,3-propanesultone (PS), propenesultone, ethylene sulfite, 1,4-butanesultone, methyl methanesulfonate, ethyl methanesulfonate, dimethyl methanedisulfonate, diethyl methanedisulfonate, dipropyl methanedisulfonate, bis(trifluoromethyl) methanedisulfonate, bis(trimethylsilyl) methanedisulfonate, methylene methanedisulfonate, ethylene methanedisulfonate, propylene methanedisulfonate, methylene ethylenedisulfonate, ethylene ethylenedisulfonate, dimethyl ethanedisulfonate, diethyl ethanedisulfonate, bis(trifluoromethyl) ethanedisulfonate, bis(trimethylsilyl) ethanedisulfonate, dimethyl propanedisulfonate, diethyl propanedisulfonate, methylene propanedisulfonate, ethylene propanedisulfonate, dimethyl 1,5-naphthalenedisulfonate, dimethyl butanedisulfonate, diethyl butanedisulfonate, 5-vinyl-hexahydro-1,3,2-benzodioxathiol-2-oxide, 1,4-butanediol dimethanesulfonate, 1,3-butanediol dimethanesulfonate, N,N-dimethylmethanesulfoneamide, N,N-diethylmethanesulfoneamide, divinylsulfone and 1,2-bis(vinylsulfonyl)methane may, for example, be mentioned.

As the cyclic acid anhydride, carboxylic anhydrides such as glutaric anhydride, maleic anhydride, citraconic anhydride, glutaconic anhydride, itaconic anhydride, succinic anhydride, diglycolic anhydride, cyclohexanedicarboxylic anhydride, cyclopentanetetracarboxylic dianhydride, 4-cylohexene-1,2-dicarboxylic anhydride, 3,4,5,6-tetrahydrophthalic anhydride, 5-norbornene-2,3-dicarboxylic anhydride, phenylsuccinic anhydride, 2-phenylglutaric anhydride, phthalic anhydride, pyromellitic anhydride, fluorosuccinic anhydride and tetrafluorosuccinic anhydride, trifluoromethanesulfonic anhydride, 1,2-ethanedisulfonic anhydride, 1,3-propanedisulfonic anhydride, 1,4-butanedisulfonic anhydride, 1,2-benzenedisulfonic anhydride, tetrafluoro-1,2-ethanedisulfonic anhydride, hexafluoro-1,3-propanedisulfonic anhydride, octafluoro-1,4-butanedisulfonic anhydride, 3-fluoro-1,2-benzenedisulfonic anhydride, 4-fluoro-1,2-benezenedisulfonic anhydride and 3,4,5,6-tetrafluoro-1,2-benzenedisulfonic anhydride may, for example, be mentioned.

As the carboxylic acid compound, lithium oxalate, lithium malonate, lithium difluoromalonate, lithium succinate, lithium tetrafluorosuccinate, lithium adipate, lithium glutarate, lithium acetonedicarboxylate, lithium 2-oxobutyrate, lithium oxaloacetate, lithium 2-oxoglutarate, lithium acetoacetate, lithium 3-oxocylobutanecarboxylate, lithium 3-oxocyclopentanecarboxylate, lithium 2-oxovalerate, lithium pyruvate, lithium glyoxylate, lithium 3,3-dimethyl-2-oxobutyrate, lithium 2-hydroxypropionate, lithium 2-methyl lactate, lithium tartrate, lithium cyanoacetate, lithium 2-mercaptopropionate, lithium methylenebis(thioglycolate)thiodisuccinate, lithium 3-(methylthio)propionate, lithium 3,3'-thiodipropionate, lithium dithiodiglycolate, lithium 2,2'-thiodiglycolate, lithium thiazolidine-2,4-dicarboxylate and lithium acetylthioacetate may, for example, be mentioned.

As the boron-containing compound, $LiBF_2(C_2O_4)$, $LiB(C_2O_4)_2$, $LiBF_2(CO_2CH_2CO_2)$, $LiB(CO_2CH_2CO_2)_2$, $LiB(CO_2CF_2CO_2)_2$, $LiBF_2(CO_2CF_2CO_2)$, $LiBF_3(CO_2CH_3)$, $LiBF_3(CO_2CF_3)$, $LiBF_2(CO_2CH_3)_2$, $LiBF_2(CO_2CF_3)_2$, $LiBF(CO_2CH_3)_3$, $LiBF(CO_2CF_3)_3$, $LiB(CO_2CH_3)_4$, $LiB(CO_2CF_3)_4$, $Li_2B_2O_7$ and $Li_2B_2O_4$ may, for example, be mentioned.

Each of the above other additives may be used anole or in combination of two or more. Further, in a case where the additive is added in the non-aqueous electrolytic solution, the content of the additive in the non-aqueous electrolytic solution is preferably from 0.01 to 5 mass %, more preferably from 0.1 to 2 mass %, although it depends on the additive.

<Storage Device>

The non-aqueous electrolytic solution of the present invention may be used for various storage devices such as a lithium ion secondary battery, an electric double layer capacitor, and a hybrid battery of which one of the positive electrode and the negative electrode is a battery and the other electrode is a double layer. Now, as a representative example, a lithium ion secondary battery will be described.

As the anode active material constituting the negative electrode, any one of a carbon material capable of doping and undoping lithium ions, metal lithium, a lithium-containing alloy, silicon which can be alloyed with lithium, a silicon alloy, tin, a tin alloy, tin oxide capable of doping and undoping lithium ions, silicon oxide, a transition metal oxide capable of doping and undoping lithium ions, a transition metal nitride compound capable of doping and undoping lithium ions, and a mixture thereof may be used. The negative electrode commonly has a constitution such that an anode active material is formed on a current collector such as a copper foil or an expanded metal.

In order to improve adhesion of the anode active material to the current corrector, a binder such as a polyvinylidene fluoride binder or a latex binder may be incorporated, or carbon black, amorphous whisker carbon or the like as an electrically conducting aid may be added.

As a carbon material constituting the anode active material, for example, pyrolytic carbon, coke (such as pitch coke, needle coke, petroleum coke), graphite, an organic polymer fired product (carbonized phenol resin, furan resin or the like fired at an appropriate temperature), carbon fibers and activated carbon may, for example, be mentioned. The carbon material may be graphitized one.

The carbon material is particularly preferably a carbon material having interplanar spacing (d002) of (002) plane measured by X-ray diffraction of at most 0.340 nm, and preferably graphite having a true density of at least 1.70 g/cm$^3$ or a highly crystalline carbon material having properties close to those of the graphite. By using such a carbon material, the energy density of the non-aqueous electrolyte battery can be increased.

Further, the above carbon material containing boron, coated with a metal such as gold, platinum, silver, copper, Sn or Si (for example, boric acid-containing carbon material), or coated with amorphous carbon (for example, magnesium salt-coated carbon material or calcium salt-coated carbon material) may, for example, be used. Such carbon materials may be used alone or as a mixture of two or more in combination.

Further, silicon which can be alloyed with lithium, a silicon alloy, tin, a tin alloy, tin oxide capable of doping and undoping lithium ions, silicon oxide and a transition metal oxide capable of doping and undoping lithium ions, have a theoretical capacity per weight higher than the above carbon material and are thereby suitable.

On the other hand, the cathode active material constituting the positive electrode may be formed of various materials capable of charging and discharging. For example, a lithium-containing transition metal oxide, a lithium-containing transition metal composite oxide using at least one type of transition metal, a transition metal oxide, a transition metal sulfide, a metal oxide and an olivine metal lithium salt may be mentioned. For example, a composite oxide (lithium/transition metal composite oxide) of lithium and at least one type of transition metal represented by Li$_x$MO$_2$ (wherein M is at least one type of transition metal, and x varies depending upon the battery charged/discharged state and is usually 0.05≤x≤1.20) such as LiCoO$_2$, LiNiO$_2$, LiMn$_2$O$_4$ or LiMnO$_2$, or a metal composite oxide having part of a transition metal atom mainly constituting the lithium/transition metal composite oxide substituted with other metal such as Al, Ti, V, Cr, Mn, Fe, Co, Li, Ni, Cu, Zn, Mg, Ga, Zr, Si or Yb, chalcogenide of a transition element such as FeS$_2$, TiS$_2$, V$_2$O$_5$, MoO$_3$ or MoS$_2$, or a polymer such as polyacetylene or polypyrrole may be used. Particularly, a lithium/transition metal composite oxide capable of doping and undoping Li and a metal composite oxide material having part of a transition metal atom substituted with other metal are preferred.

Further, such a cathode active material having a material differing in the composition from the material constituting the cathode active material as the main body, attached to the surface, may also be used. As the material attached to the surface, oxides such as aluminum oxide, silicon oxide, titanium oxide, zirconium oxide, magnesium oxide, calcium oxide, boron oxide, antimony oxide and bismuth oxide; sulfates such as lithium sulfate, sodium sulfate, potassium sulfate, magnesium sulfate, calcium sulfate and aluminum sulfate; and carbonates such as lithium carbonate, calcium carbonate and magnesium carbonate may, for example, be mentioned.

The positive electrode commonly has a constitution such that a cathode active material is formed on a current collector such as an aluminum, titanium or stainless steel foil or an expanded metal. In order to improve adhesion of the cathode active material to the current corrector, a binder such as a polyvinylidene fluoride binder or a latex binder may be incorporated, and in order to improve electron conductivity in the positive electrode, carbon black, amorphous whisker, graphite or the like may be incorporated.

The separator is preferably a membrane which electrically insulates the positive electrode and the negative electrode and which has lithium ion permeability, and may, for example, be a porous membrane such as a microporous polymer film. The microporous polymer film is particularly preferably a porous polyolefin film, more specifically, preferably a porous polyethylene film, a porous polypropylene film or a multilayer film of a porous polyethylene film and a polypropylene film. Further, as the separator, a polymer electrolyte may be used. The polymer electrolyte may, for example, be a polymer substance having a lithium salt dissolved therein or a polymer substance swollen by an electrolytic solution, but is not limited thereto.

The non-aqueous electrolytic solution of the present invention may be used for the purpose of swelling the polymer substance to obtain a polymer electrolyte, or may be infiltrated into a separator comprising a porous polyolefin film and a polymer electrolyte used in combination.

The shape of the lithium ion secondary battery using the non-aqueous electrolytic solution of the present invention is not particularly limited, and the battery may be formed into e.g. cylindrical, rectangular, aluminum laminate, coin or button batteries.

EXAMPLES

Now, the present invention will be described in further detail with reference to Examples. However, it should be understood that the present invention is by no means restricted thereto, and modifications are possible within the scope of the present invention.

<Preparation of Electrolytic Solutions 1-1 to 1-12>

In a mixed solvent of ethylene carbonate (EC), ethyl methyl carbonate (EMC) and fluoroethylene carbonate (FEC) (volume ratio of 30:68:2), LiPF$_6$ as a lithium salt was dissolved at a concentration of 1 mol/liter to prepare standard electrolytic solution 1-1.

Then, to the standard electrolytic solution 1-1, the organic sulfone compounds as identified in Table 1 were added in contents as identified in Table 1 to prepare electrolytic solutions 1-2 to 1-12. The content (%) in Table 1 is mass % to the total mass (100 mass %) of the standard electrolytic solution 1-1 and the organic sulfone compound.

TABLE 1

| Electrolytic solution | Organic sulfone compound | Content (%) |
|---|---|---|
| 1-1 | Nil | |
| 1-2 | (CH$_2$=CH—SO$_2$—CH$_2$)$_2$—(CH)OC(=O)CH$_3$ | 1.0 |

TABLE 1-continued

| Electrolytic solution | Organic sulfone compound | Content (%) |
|---|---|---|
| 1-3 | $(CH_2=CH-SO_2-CH_2)_2-(CH)OC(=O)CF_3$ | 1.0 |
| 1-4 | $(CH_2=CH-SO_2-CH_2)_2-(CH)OS(=O)_2CH_3$ | 1.0 |
| 1-5 | $(CH_2=CH-SO_2-CH_2)_2-(CH)OS(=O)_2CF_3$ | 1.0 |
| 1-6 | $(CH_2=CH-SO_2-CH_2)_2-(CH)OSi(CH=CH_2)(CH_3)_2$ | 1.0 |
| 1-7 | $(CH_2=CH-SO_2-CH_2)_2-(CH)OSi(CH_3)_3$ | 0.5 |
| 1-8 | $(CH_2=CH-SO_2-CH_2)_2-(CH)OSi(CH_3)_3$ | 1.0 |
| 1-9 | $(CH_2=CH-SO_2-CH_2)_2-(CH)OSi(CH_3)_3$ | 2.0 |
| 1-10 | $(CH_2=CH-SO_2-CH_2)_2-(CH)OP(=O)(OSi(CH_3)_3)_2$ | 1.0 |
| 1-11 | $(CH_2=CH-SO_2-CH_2)_2-(CH)OB(OSi(CH_3)_3)_2$ | 1.0 |
| 1-12 | $(CH_2=CH-SO_2-CH_2)_2-CH_2OH$ | 1.0 |

<Preparation of Electrolytic Solutions 2-1 to 2-4>

$(CH_2=CH-SO_2-CH_2)_2-CH_2OSO_2CF_3$ was added in an amount of 0.5 mass % to the standard electrolytic solution 1-1 (99.5 mass %), and dissolved to prepare standard electrolytic solution.

Then, to the above standard electrolytic solution, compounds as identified in Table 2 were added in contents as identified in Table 2 to prepare electrolytic solutions 2-1 to 2-4. The content (%) of the additive as identified in Table 2 is mass % to the total mass (100 mass %) of the standard electrolytic solution and the additive.

TABLE 2

| Electrolytic solution | Additive | Content (%) |
|---|---|---|
| 2-1 | Vinylene carbonate | 1.0 |
| 2-2 | 1,3-propanesultone | 1.0 |
| 2-3 | Maleic anhydride | 0.5 |
| 2-4 | Lithium oxalate | 0.5 |

<Preparation of Battery>

A flat wound electrode group having a positive electrode comprising an aluminum current collector coated with a positive electrode material and a negative electrode comprising a copper current collector coated with a negative electrode material wound via a separator (F23DHA, manufactured by Toray Battery Separator Film Co., Ltd.) having a thickness of 23 μm, was accommodated in a case to prepare a rectangular battery cell of 30 mm×30 mm×2.0 mm in thickness.

The positive electrode was prepared in such a manner that to a positive electrode material obtained by mixing 5 mass % of polyvinylidene fluoride as a binder, 4 mass % of acetylene black as an electrically conductive material, and 91 mass % of $LiNi_{0.5}Mn_{0.3}Co_{0.2}O_2$ as a cathode active material which is a composite oxide powder of lithium, nickel, manganese and cobalt, N-methylpyrrolidone was added to prepare a paste, which was applied to both surfaces of an aluminum foil current collector having a thickness of 18 μm, the solvent was removed by drying, and the aluminum foil current collector was calendered by a roll press.

The negative electrode was prepared in such a manner that 95.8 mass % of an artificial graphitized carbon powder, 2.0 mass % of a styrene butadiene rubber (SBR) as a binder and a carboxymethyl cellulose 2.2 mass % aqueous solution were mixed, and formed into a slurry with water as a dispersion medium, the slurry was applied on both sides of a copper foil having a thickness of 12 μm, the solvent was removed by drying, and the copper foil was calendered by a roll press. As the separator, a polyethylene microporous film was used.

Then, using the above prepared battery cell, a battery was prepared in the following procedure.

a. 0.55 g of an electrolytic solution was weighed and poured into an inlet of the battery cell, followed by decompression, and the inlet was sealed.

b. The sealed battery cell was charged at 8 mA to 4.2 V and then discharged at 8 mA to 3.0 V in a 45° C. atmosphere.

c. The gas inside the battery cell discharged to 3.0 V was removed under reduced pressure to prepare a battery.

<Evaluation of Battery>

Of the above prepared battery, properties were measured as follows.

a. Resistance Change

Before the following high temperature cycle test, the battery was charged at 25° C. to SOC (state of charge) 50%, and discharged at 0.2 C, 0.5 C, 1.0 C or 2.0 C in each environment for 10 seconds to obtain an initial direct current resistance.

The battery was charged in a 45° C. atmosphere at 1 C rate to 4.2 V and then discharged in the same atmosphere at 1 C rate to 3.0 V, and such a cycle was repeated 200 times, and then the direct current resistance after cycles was obtained under the same conditions as before the high temperature cycle test. From the initial direct current resistance and the direct current resistance after cycles, the resistance change was obtained in accordance with the following formula.

$$\text{Resistance change (\%)} = (\text{resistance after cycles/initial resistance}) \times 100 \quad (1)$$

b. Capacity Retention

The battery was charged in a 45° C. atmosphere at 1 C rate to 4.2 V and then discharged in the same atmosphere at 1 C rate to 3.0V, and the discharge capacity was taken as the initial capacity. Such a cycle was repeated 200 times under the same conditions, and the discharge capacity at the 200th cycle was taken as the capacity after cycles. From the initial capacity and the capacity after cycles, the capacity retention was obtained in accordance with the following formula.

$$\text{Capacity retention (\%)} = (\text{capacity after cycles/initial capacity}) \times 100 \quad (2)$$

c. Volume Change

In a 25° C. atmosphere, a predetermined amount of pure water was weighed in a beaker, and the entire laminate battery was sunk in the water, and the amount of the volume increased in the beaker was weighed, and the amount increased was taken as the initial volume of the laminate battery. Then, under the same conditions, the amount of the volume increased of a laminate battery which had been charged in a 25° C. atmosphere at 0.2 C rate to 4.2 V and left to stand in a 60° C. atmosphere for 14 days, was weighed, which was taken as the volume after storage of the laminate battery. From the initial volume and the volume after storage, the volume change was obtained in accordance with the following formula.

$$\text{Volume change (\%)} = (\text{volume after storage/initial volume}) \times 100 \quad (3)$$

Examples 1 to 14

Using each of the electrolytic solutions 1-1 to 1-11 as identified in Table 1 and the electrolytic solutions 2-1 to 2-4 as identified in Table 2, in accordance with the above battery preparation procedure, laminate batteries in Examples 1 to 13 and Comparative Example 1 were prepared, and the initial resistance was obtained in a 25° C. atmosphere.

Then, in a 45° C. atmosphere, a cycle of charging at 1 C rate to 4.2 V and discharging to 3.0 V was repeatedly carried out 200 times, and the capacity retention was obtained from the initial capacity and the discharge capacity after 200 cycles, and the direct current resistance after cycles was obtained in the same manner, and the resistance change was obtained from the initial resistance and the direct current resistance after 200 cycles. The results are shown in Table 3.

TABLE 3

| Examples | Electrolytic solution | Capacity retention (%) | Resistance change (%) |
|---|---|---|---|
| 1 | 1-2 | 89 | 116 |
| 2 | 1-3 | 90 | 114 |
| 3 | 1-4 | 90 | 110 |
| 4 | 1-5 | 91 | 109 |
| 5 | 1-6 | 90 | 112 |
| 6 | 1-7 | 88 | 120 |
| 7 | 1-8 | 90 | 117 |
| 8 | 1-9 | 90 | 112 |
| 9 | 1-10 | 90 | 110 |
| 10 | 1-11 | 89 | 111 |
| 11 | 2-1 | 91 | 112 |
| 12 | 2-2 | 93 | 107 |
| 13 | 2-3 | 92 | 110 |
| 14 | 2-4 | 93 | 104 |
| Comparative Example 1 | 1-1 | 87 | 142 |

As shown in Table 3, by adding the organic sulfone compound of the present invention, the increase of the direct current resistance after high temperature cycles can be remarkably reduced. It is considered that the organic sulfone compound, which has element of e.g. sulfur, phosphorus or boron in its structure, is likely to form a dense coating film on the surface of the active material, and suppresses decomposition of the electrolytic solution component, whereby the increase of the resistance can be remarkably reduced. Further, by adding the additive, the increase of the resistance can further be suppressed. In addition, an effect to improve the capacity retention after cycles is obtained.

Examples 15 to 17

Using each of the electrolytic solutions 1-12, 1-2, 1-4 and 1-10 as identified in Table 1, in accordance with the above battery preparation procedure, laminate batteries in Examples 15 to 17 and Comparative Example 2 were prepared, and the initial resistance was obtained in a 25° C. atmosphere, and the initial volume of each battery was obtained.

Then, each battery was charged in a 25° C. atmosphere at 0.2 C rate to 4.2 V, and left to stand in a 60° C. atmosphere for 14 days.

The battery was returned to 25° C., and the resistance after storage and the volume after storage were obtained in the same manner as above, and the resistance change and the volume change relative to the initial values were obtained. The results are shown in Table 4.

TABLE 4

| Examples | Electrolytic solution No. | Resistance change (%) | Volume change (%) |
|---|---|---|---|
| 15 | 1-2 | 117 | 123 |
| 16 | 1-4 | 112 | 119 |
| 17 | 1-10 | 115 | 117 |
| Comparative Example 2 | 1-12 | 137 | 176 |

As shown in Table 4, by adding the organic sulfone compound of the present invention, the increase of the direct current resistance and the volume change after storage at high temperature can be remarkably reduced.

INDUSTRIAL APPLICABILITY

The non-aqueous electrolytic solution for a storage device of the present invention is widely used for storage devices, e.g. power sources for consumer equipment such as mobile phones and notebook computers, power sources for industrial equipment, storage batteries and power sources for automobile.

The invention claimed is:

1. A non-aqueous electrolytic solution for a storage device having an electrolyte dissolved in a non-aqueous solvent, wherein the electrolyte is a lithium salt soluble in the non-aqueous solvent, and the non-aqueous electrolytic solution contains an organic sulfone compound represented by the following formula (1):

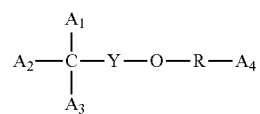

(1)

wherein $A_1$, $A_2$, and $A_3$ are each independently —X—SO$_2$—CH=CH$_2$, a hydrogen atom, a substituted or non-substituted $C_{1-5}$ alkyl group, alkenyl group, alkynyl group or alkoxy group, a substituted or non-substituted $C_{6-10}$ aryl group, or —O—SiR'$_1$R'$_2$R'$_3$ wherein R'$_1$R'$_2$ and R'$_3$ are each independently a hydrogen atom, a substituted or non-substituted $C_{1-5}$ alkyl group, provided that at least one of $A_1$, $A_2$, and $A_3$ is —X—SO$_2$—CH=CH$_2$, wherein $A_4$ is a hydrogen atom, a substituted or non-substituted $C_{1-5}$ alkyl group, alkenyl group, alkynyl group or alkoxy group, a substituted or non-substituted $C_{6-10}$ aryl group, or —O—SiR'$_1$R'$_2$R'$_3$ wherein R'$_1$, R'$_2$ and R'$_3$ are each independently a hydrogen atom, a substituted or non-substituted $C_{1-5}$ alkyl group, X and Y are each independently a single bond, a substituted or non-substituted phenylene group, or a substituted or non-substituted $C_{1-4}$ alkylene group, R is selected from the following groups:

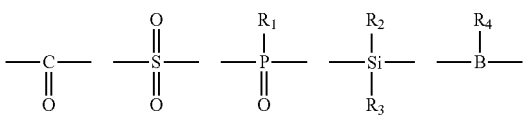

wherein $R_1$, $R_2$, $R_3$ and $R_4$ are each independently a hydrogen atom, a substituted or non-substituted $C_{1-5}$ alkyl group, alkenyl group, alkynyl group or alkoxy group, a substituted or non-substituted $C_{6-10}$ aryl group, or —O—$SiR'_1R'_2R'_3$ wherein $R'_1$, $R'_2$ and $R'_3$ are as defined above.

2. The non-aqueous electrolytic solution for a storage device according to claim 1, wherein R in the formula (1) is selected from the following groups:

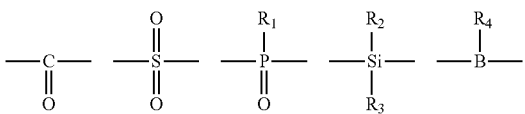

wherein $R_1$ is a substituted or non-substituted $C_{1-5}$ alkyl group, alkenyl group, alkynyl group or alkoxy group, or —O—$SiR'_1R'_2R'_3$ wherein $R'_1$, $R'_2$ and $R'_3$ are as defined in claim 1, and $R_2$ and $R_3$ are each independently a substituted or non-substituted $C_{1-5}$ alkyl group or alkoxy group, or a vinyl group, and $R_4$ is s substituted or non-substituted $C_{1-5}$ alkyl group, alkenyl group, alkynyl group or alkoxy group, or —O—$SiR'_1R'_2R'_3$ wherein $R'_1$, $R'_2$, and $R'_3$ are as defined above.

3. The non-aqueous electrolytic solution for a storage device according to claim 1, wherein $A_1$ and $A_2$ are —X—$SO_2$—CH=$CH_2$.

4. The non-aqueous electrolytic solution for a storage device according to claim 1, wherein Y is a single bond.

5. The non-aqueous electrolytic solution for a storage device according to claim 1, wherein X is a substituted or non-substituted $C_{1-4}$ alkylene group.

6. The non-aqueous electrolytic solution for a storage device according to claim 1, which contains from 0.0001 mass % to 10 mass % of the organic sulfone compound.

7. The non-aqueous electrolytic solution for a storage device according to claim 1, wherein the non-aqueous solvent contains a chain carbonic acid ester, a saturated cyclic carbonic acid ester and an unsaturated cyclic carbonic acid ester.

8. The non-aqueous electrolytic solution for a storage device according to claim 7, which has chain carbonic acid ester, saturated cyclic carbonic acid ester and unsaturated cyclic carbonic acid ester contents of from 30 mass % to 80 mass %, from 10 mass % to 50 mass % and from 0.01 mass % to 5 mass %, respectively.

9. The non-aqueous electrolytic solution for a storage device according to claim 1, wherein the lithium salt is at least one lithium salt selected from the group consisting of $LiPF_6$, $LiBF_4$, $LiCF_3SO_3$, $LIN(FSO_2)_2$, $LiN(CF_3SO_2)_2$, $LiN(C_2F_5SO_2)_2$, $LiN(CF_3SO_2)(C_2F_5SO_2)$, and $LiN(CF_3SO_2)(C_4F_9SO_2)$.

10. The non-aqueous electrolytic solution for a storage device according to claim 1, which further contains at least one additive selected from the group consisting of
- a sulfur-containing compound, excluding the organic sulfone compound represented by the formula (1),
- a cyclic acid anhydride,
- a carboxylic acid compound,
- a silicon-containing compound, and
- a boron-containing compound.

11. A storage device using the non-aqueous electrolytic solution as defined in claim 1.

12. The storage device according to claim 11, which is a lithium secondary battery.

* * * * *